United States Patent [19]

Raffalski

[11] Patent Number: 4,687,343

[45] Date of Patent: Aug. 18, 1987

[54] DEFORMATION DILATOMETER PLATENS

[75] Inventor: Karl-Heinz Raffalski, Wheatley Heights, N.Y.

[73] Assignee: Theta Industries, Inc., Port Washington, N.Y.

[21] Appl. No.: 530,502

[22] Filed: Sep. 9, 1983

[51] Int. Cl.⁴ .......................................... G01N 25/16
[52] U.S. Cl. ...................................... 374/56; 374/51
[58] Field of Search ............................ 374/55, 56, 51; 336/136; 73/818, 822, 825

[56] References Cited

U.S. PATENT DOCUMENTS

| 2,278,416 | 4/1942 | Atti | 73/818 |
| 3,234,778 | 2/1966 | Kreglo, Jr. | 374/51 |
| 3,545,263 | 12/1970 | Hadley et al. | 73/825 |
| 3,805,589 | 4/1974 | Clusener et al. | 374/56 |
| 3,842,654 | 10/1974 | Bechtel | 374/51 |
| 3,898,836 | 8/1975 | Clusener | 374/56 |
| 4,186,044 | 1/1980 | Bradley et al. | 219/10.55 A |
| 4,351,615 | 9/1982 | Rodriques | 374/56 |

FOREIGN PATENT DOCUMENTS

| 958848 | 5/1964 | United Kingdom | 374/55 |
| 224394 | 10/1968 | U.S.S.R. | 374/55 |
| 932365 | 10/1980 | U.S.S.R. | 73/818 |

OTHER PUBLICATIONS

Pollack H. W., "Materials Science and Metallurgy", Second Edition, Reston Publishing Co. Inc., Reston, Va., 1977, pp. 326-331.
Keyser, Carl A., "Materials Science in Engineering", Second Edition, Charles E. Merrill Publishing Co., Columbus, Ohio, 1974, pp. 270-273.
Recoding Quartz Differential Dilatometer by Lloyd Argonne, National Laboratory, Jul. 1959.
An Apparatus for Determining the Coefficient of Thermal Expansion of Rocks, Mortar and Concretes, by Loubser et al., Magazine of Concrete Research, vol. 24, No. 79, Jun. 1972.

Primary Examiner—Charles Frankfort
Assistant Examiner—Thomas B. Will
Attorney, Agent, or Firm—Burton E. Levin

[57] ABSTRACT

Deformation dilatometers are described for heating, deforming and cooling a test specimen, as well as for measuring changes in the linear dimensions of that specimen. A ferrous metal specimen, that is held between a fixed and a movable fused silica or quartz platen, first is heated by a high frequency induction coil and then crushed by the application of a hydraulic force to the movable platen. The hydraulic force then is withdrawn and, as the specimen is cooled by a jet of quenching gas, changes in its linear dimension are measured by a linear variable differential transformer which is coupled through ceramic pushrods to the platens. Use of fused silica or quartz platens in deformation dilatometers permits the accurate simulation of steel mill forging and rolling operations and enhances the usefulness of the instruments for studying phase changes in steel and determining optimum heating and quenching rates.

15 Claims, 3 Drawing Figures

FIG. 1
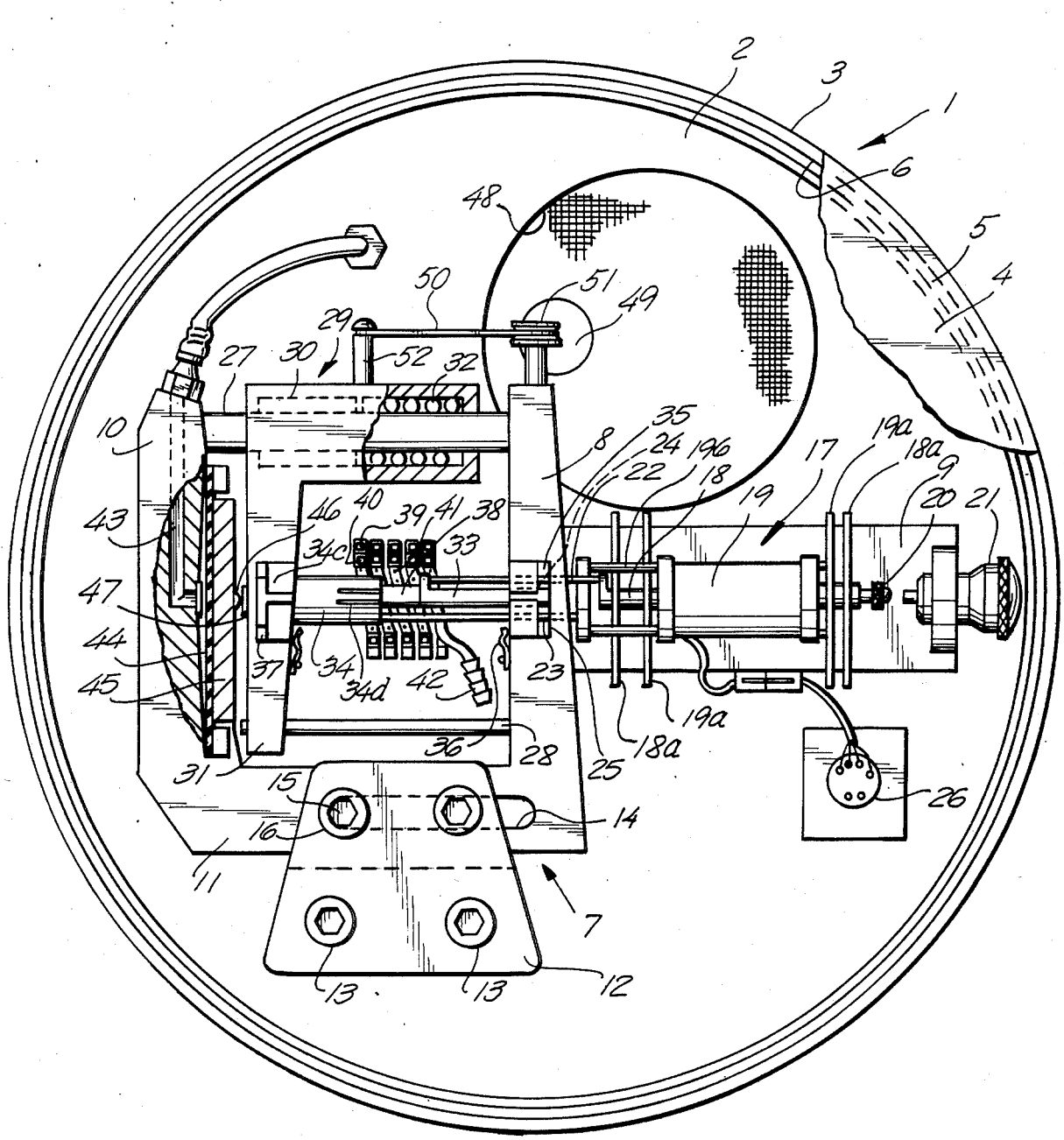
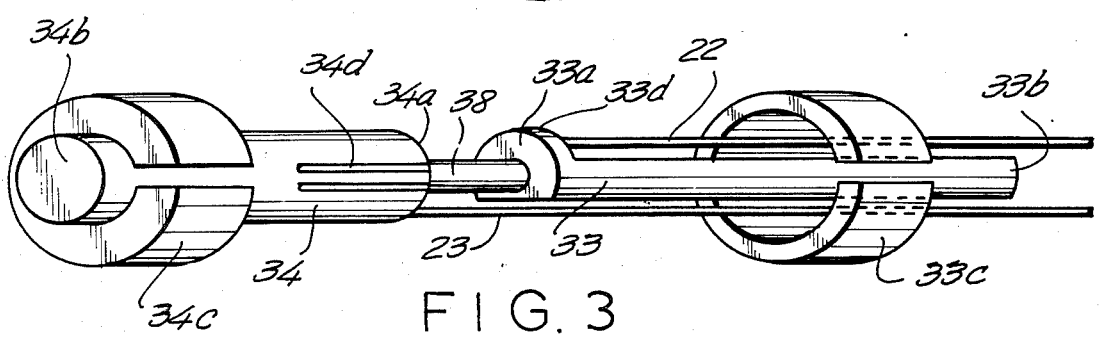
FIG. 3

DEFORMATION DILATOMETER PLATENS

BACKGROUND OF THE INVENTION

1. Field of the Invention

This invention relates generally to dilatometers and, more particularly, to improved test specimen support platens which can be used to transmit a deforming force to the specimen and, when the deforming force is absent, also can be used to transmit thermally induced changes in the linear dimensions of the specimen to the dilatometer sensor.

2. Description of the Prior Art

Dilatometers are analytical instruments that respond to the linear thermal expansion or contraction of solids. Typically, these instruments have a variable temperature furnace in which the test specimen rests between a flat surface on a stationary object and an opposing flat surface on a movable object, such as a ceramic rod, that extends outside the furnace. Temperature induced changes in the length of the specimen are transmitted through the rod to a mechanical, optical or electrical system for amplifying and measuring that change. These instruments can be used to make precise measurements of changes in length resulting from small temperature changes or to plot variations in the rate of linear expansion or contraction over a broad temperature range. Such measurements are invaluable in studying the compatibility under changing temperature conditions of different materials which are bonded together or are in close contact; e.g., metal to glass, enamel to substrates, thin film deposits in microcurcuits or metal or plastic fillings in natural teeth. Exemplary of the dilatometers that are commonly used for such applications are the instruments described in U.S. Pat. Nos. 3,680,357 and 3,898,836.

Dilatometers also can be used to detect and measure the precise temperature at which phase transitions occur in a specimen material. One such application is the study of the crystalline structure of steel and the effect on that structure of the heating and cooling rates to which it has been subjected. By simulating various steel mill operating capabilities, it is possible to determine the optimum heating or cooling rate for a specific alloy which will result in a product having desired properties or combinations of properties. A dilatometer designed specifically for this purpose is described in U.S. Pat. No. 3,805,589. In this instrument, linear dimensional changes of the specimen are transmitted through a ceramic push rod to the independently suspended core of a linear variable differential transformer that converts these dimensional changes to electric signals. When amplified and plotted against temperature and time, these signals clearly show phase changes. Variable rates and intensities of heating of the specimen are effected by controlling the current fed to an induction coil wound about the specimen and variable rates and intensities of cooling are effected by controlling the volume of a jet of quenching fluid, such as helium, that is directed either into a passageway through the specimen or on its outer surface. Although this quenching dilatometer accurately simulates steel mill production of cast products and is widely used to determine optimum heating and cooling rates, it does not fully reflect the effect of forging or rolling on transition temperatures or crystal structure.

In order to simulate these common steel mill deforming operations, conventional quenching dilatometers have been modified to provide the capability of crushing the specimen between the heating and quenching stages, as illustrated by the pioneer model deformation dilatometer described by Smith and Siebert, "Transformation Kinetics of Thermomechanically Worked Austenite by Deformation Dilatometry", Applications of Modern Metallographic Techniques, ASTM STP 480, American Society for Testing and Materials, 1970, pp. 131-151. Specimen deformation is accomplished with this instrument by holding the cylindrical specimen vertically between a flat smooth surface on a lower fixed corderite platen and a parallel opposed flat smooth surface on an upper movable corderite platen. After the specimen is heated, a deforming force is applied, via a hydraulic cylinder, to the movable platen normal to and in the direction of its flat smooth surface that is in contact with the specimen. After withdrawal of the deforming force, the specimen is quenched with a jet of helium and further dimensional changes are transmitted to the core of a linear variable differential transformer through a pushrod that rests on the movable platen.

While this early deformation dilatometer led to a much improved understanding of the effect of forging or rolling on the crystalline structure of steel, the data produced often was distorted by dimensional changes occurring in the corderite platens and the instrument was of limited use in identifying optimum heating and cooling cycles for steel mill forging or rolling operations.

In response to this recognized shortcoming, more sophisticated versions of the deformation dilatometer were developed which automatically compensate for thermally induced dimensional changes in the corderite platens by employing two pushrods, each of which is coupled to a different element (core or coil) of a linear variable differential transformer in which these elements are independently movable. One of these pushrods abuts the flat smooth surface of the movable platen adjacent the specimen and is responsive to the cumulative linear expansion or contraction of the specimen and the fixed platen. The second pushrod, which is coupled to the other independently movable element of the linear variable differential transformer, abuts a lip adjacent the specimen bearing surface of the fixed platen and, being responsive to only the linear expansion or contraction of the fixed platen, cancels the electrical output reflecting that dimensional change.

While the elimination of this platen error greatly improved the accuracy of the deformation dilatometer for many laboratory measurements, the continued frequent occurrence of erroneous results and the difficulty of identifying same has limited the widespread use of this instrument to establish optimum heating and cooling cycles for steel mill forging and rolling operations. Prior to this invention, the cause of these erratic results was not understood and could not be avoided.

SUMMARY OF THE INVENTION

The present invention arose from applicant's observations that when steel specimens are deformed at high temperature between corderite platens, there often is a microscopically visible migration of both platen and specimen material across the interface and that this occurrence invariably results in anomalous dilatometer readings. This migration is believed to introduce an extraneous alloy at the interface which may temporarily weld or otherwise bond the specimen to the platen. The anomalous dilatometer readings that are obtained during quenching of a specimen that has been subjected to such migration are believed to reflect the contraction of the extraneous alloy and the breaking of the temporary weld, as well as the contraction of a shortened specimen.

Applicant also has discovered that material migration across the interface of a steel specimen and a deformation dilatometer platen can be avoided by employing fused silica or quartz at at least the surface of the platen which is in contact with the specimen, and that this simple expedient dramatically and unexpectedly improves the accuracy and reliability of a deformation dilatometer and extends the life of the platens.

One aspect of applicant's invention is an improved deformation dilatometer platen having a smooth flat surface adapted to abut a dilatometer specimen, at least said smooth flat surface being made of fused silica or quartz.

Another aspect of applicant's invention is a deformation dilatometer of improved accuracy comprising:

(a) a linear variable differential transformer including an axially movable core coupled to a pushrod, an axially movable coil coupled to a separate pushrod and means for separately supporting each of said core and coil to permit independent axial movement thereof, (b) a pair of spaced apart platens having opposed parallel flat fused silica or quartz surfaces for supporting a test specimen therebetween, one said platen being fixed and the other said platen being movable normal to said opposed parallel surfaces, one said pushrod being responsive to the cumulative linear expansion or contraction of said fixed platen and said specimen and the other said pushrod being responsive to the linear expansion or contraction of said fixed platen and (c) means for selectively applying a controlled specimen deforming force or a lesser non-deforming force to said movable platen in a direction normal to and toward said opposed parallel surfaces.

Still another aspect of applicant's invention is an improved process for determining phase changes occurring during cooling of a mechanically worked ferrous metal specimen comprising:

(a) holding said specimen between opposed parallel flat surfaces of a fixed platen and a movable platen, said parallel flat surfaces being made of fused silica or quartz, (b) deforming said specimen by applying a deforming force to said movable platen normal to and toward said parallel flat surfaces, (c) reducing said force to a positive non-deforming level and (d) measuring the relative movement of said parallel flat surfaces while cooling said specimen.

BRIEF DESCRIPTION OF THE DRAWINGS

FIG. 1 is a schematic plan view, partially broken away and partially in section, illustrating a preferred embodiment of a deformation dilatometer of this invention.

FIG. 3 is a schematic perspective view of a pair of deformation dilatometer platens of this invention.

DESCRIPTION OF THE PREFERRED EMBODIMENTS

Figure 2:
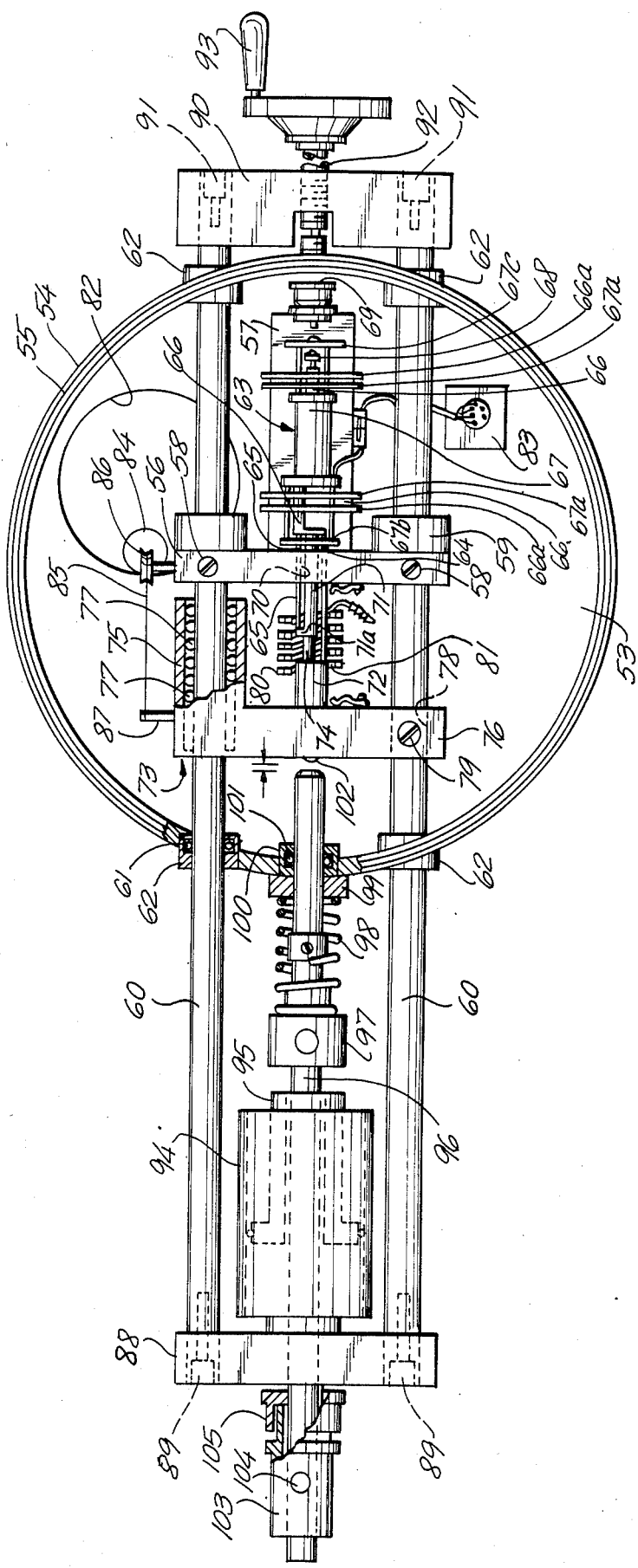
FIG. 2 is a schematic plan view, partially broken away and with a portion removed for clarity, of another preferred embodiment of a deformation dilatometer of this invention.

FIG. 1 illustrates a deformation dilatometer measuring head which is positioned entirely within a vacuum chamber 1. Vacuum chamber 1 is defined by a base plate 2, a tubular side wall 3 and a removable cover 4 which rests on O-ring 5 that is seated in groove 6 on the top edge of side wall 3 and that provides a hermetic seal. Another O-ring (not shown) similarly seals the bottom edge of side wall 3 to base plate 2.

A U-shaped bracket 7, defined by first leg 8 having an extension 9, second leg 10 and connecting leg 11, is mounted on the base plate 2 by means of bracket 12 and fasteners 13. The connecting leg 11 is slotted, as shown by reference character 14, in order to receive clamping screws 15 and washers 16. By this construction, bracket 7 may be moved to the left or right in order to load and unload the test specimen, as will be described more fully below.

The core 18 and coil 19 of a conventional linear variable differential transformer 17 are separately mounted on extension 9 of leg 8 by pairs of frictionless compound cantilevered springs 18a and 19a, respectively, to permit independent axial movement of these transformer elements. A micrometer 21 and a screw 20, each of which can be used to axially displace core 18, are provided for calibrating and electrical zeroing, respectively, the linear variable differential transformer 17. The construction of springs 18a and 19a and electrical zeroing screw 20 are generally the same as those described in U.S. Pat. Nos. 3,898,836 and 3,919,879, the disclosures of which are incorporated herein by reference. Ceramic push rods 22 and 23, which are coupled to the core 18 and coil 19 ,respectively, pass loosely through holes 24 and 25 in the first leg 8 of bracket 7. A feedthrough terminal 26 is provided in base plate 2 for electrical connections.

The U-shaped bracket 7 is provided with a first connecting rod 27 that spans legs 8 and 10. A second connecting rod 28 is cantilevered from leg 8 toward leg 10. A L-shaped bracket 29, having a first leg 30 and a second leg 31, is slidably mounted on U-shaped bracket 7. Linear ball bearings 32 support first leg 30 on first connecting rod 27 while second leg 31 is slidably mounted oh second connecting rod 28.

A first cylindrical fused silica platen 33 is secured to first leg 8 of bracket 7 and a second cylindrical fused silica platen 34, which is in coaxial opposition to first platen 33, is secured to second leg 31 of bracket 29. As seen more clearly in FIG. 3, platen 33, which has ends 33a and 33b that are parallel and that are ground flat and smooth, is encircled by an Invar split ring 33c adjacent to end 33b. Platen 34 is provided with similar parallel flat smooth ends 34a and 34b, as well as an Invar split ring 34c. Platen 33 is secured in circular depression 35 of leg 8 by spring clips 36 which are attached to leg 8 and bear on split ring 33c, thereby holding end 33b firmly against the dimensionally matching surface at the base of depression 35. Platen 34 is secured similarly in depression 37 by spring clips 36. When both platens are so secured, ends 33a and 34a are opposed and their parallel surfaces bear against opposite ends of test specimen 38. First platen 33 also has one flattened portion of its curved surface that defines a lip 33d contiguous with specimen bearing end 33a and that provides clearance for core pushrod 22 which abuts lip 33d. A second flattened portion of its curved surface provides clearance for coil pushrod 23, which bypasses platen 33 and abuts the smooth flat specimen bearing end 34a of second platen 34. Axial grooves 34d hold wire leads from a thermocouple (not shown) that is welded to the side of specimen 38.

A high frequency induction heating coil 39 and a quenching coil 40 having perforations 41 are concentrically wound about specimen 38. The induction coil 39 is connected through a suitable programmer to a source of high frequency current (neither shown) and advantageously is cooled by an internal flow of water (not shown). The quenching coil 40 is connected by fitting 42 to a programmed flow control means and a source of quenching gas, such as helium (neither shown).

When it is necessary to load or unload specimen 38, screws 15 are loosened so that the entire first bracket 7 may be moved to a position where specimen 38 and specimen bearing ends 33a and 34a of the platens move outside coils 39 and 40.

The second leg 10 of bracket 7 is provided with a passageway 43 that communicates with a hydraulic pressure source (not shown). A flexible diaphragm 44 is mounted over the outlet of passageway 43 and is covered by a disc plunger 45. A semi-spherical member 46 protrudes from the surface of plunger 45 in opposition to anvil 47 which is secured to the second leg 31 of second bracket 29.

A vacuum port 48, formed in base plate 2, communicates with a controlled source of high vacuum (not shown). A weight 49 is coupled to second bracket 29 by means of line 50 that passes over pulley 51 that is mounted on first bracket 7. Line 50 terminates at pin 52 which is secured to second bracket 29. The weight 49 adds a constant predetermined load to second bracket 29 and, except for the period of application of the hydraulic deforming force, provides the only force urging platen 34 toward platen 33 and holding specimen 38 therebetween.

In a typical test performed on the deformation dilatometer of FIG. 1, a ferrous metal test specimen 38 first is heated to a desired temperature by passing current through the induction coil 39. The specimen then is subjected to a desired degree of deformation by applying hydraulic pressure to bracket 29 and movable platen 34. Upon withdrawal of the hydraulic pressure, deformed specimen 38 is rapidly quenched by helium impinging on its surface from quenching coil 40 and its contraction, which is reflected by the relative movement of platen ends 33a and 34a is transmitted, via pushrods 22 and 23, to the linear variable differential transformer for measurement.

Another embodiment of the deformation dilatometer of this invention is illustrated by FIG. 2. This embodiment also has a vacuum enclosure comprising a base plate 53, a shell 54 having O-ring seals 55 (only one shown) and a cover (not shown). A first bracket 56 is secured, by means of screws 58 and fixed ring stops 59 to a pair of connecting rods 60 that extend through the wall of shell 54. O-rings 61, which are positioned within collars 62 that surround rods 60, provide a hermetic seal. A linear variable differential transformer 63, similar to that employed in the embodiment of FIG. 1, is mounted, through compound cantilevered springs 66a and 67a, on extension 57 of first bracket 56, and pushrods 64 and 65, which are coupled to the core 66 and coil 67, respectively, pass loosely through bores 70 in bracket 56. Micrometer 69, which can be turned to bear on yoke 67c to axially displace the coil of transformer 63, and screw 68, which can be turned to axially displace the core of the transformer, are provided for calibrating and electrical zeroing, respectively. A fixed fused silica platen 71, which is identical to the fixed platen of FIGS. 1 and 3, is secured to bracket 56 in the same manner as in FIG. 1 and is positioned coaxially with the linear variable differential transformer 63. Unlike the FIG. 1 arrangement of parts, the coil pushrod 65 abuts lip 71a on fixed platen 71 and core pushrod 64 extends past platen 71 to abut the specimen bearing end of movable fused silica platen 72.

Movable fused silica platen 72, which is identical to the movable platen of FIGS. 1 and 3, is secured to L-shaped bracket 73 in the same manner as in FIG. 1 and is positioned with its flat smooth specimen bearing end opposed to and parallel with the specimen bearing end of fixed platen 71 so as to hold a test specimen 74 therebetween. A first leg 75 of bracket 73 is slidably mounted on one of the rods 60 by means of linear ball bearings 77. The second leg 76 is provided with a bore 78 through which passes the other rod 60. Two polyfluoroethylene plugs 79, which are positioned 180° apart and are threaded into the top and bottom of second leg 76, bear against the rod 60 passing through bore 78 and can be used to vertically adjust leg 76 to accurately align the platens.

An induction heating coil 80 and a concentric quenching coil 81 are wound about test specimen 74 in the same manner as in the embodiment of FIG. 1 and are similarly connected to programmers and sources of high frequency current and quenching gas (not shown). As in the FIG. 1 embodiment, base plate 53 is provided with a vacuum port 82, which communicates with a source of high vacuum (not shown), and an electrical feedthrough terminal 83. A weight 84, which is coupled to peg 87 on the L-shaped bracket 73 by wire 85 that passes over a pulley 86 on first bracket 56, provides a constant load drawing the L-shaped bracket 73 toward first bracket 56.

An end plate 88 is secured to and rigidly couples the left ends of rods 60 by means of screws 89. A second end plate 90 is secured to and rigidly couples the right ends of rods 60 by means of screws 91. A screw 92, which is actuated by crank 93, is threaded through end plate 90 and is rotatably held at the outer surface of shell 54. Rotation of crank 93 causes axial movement of rods 60, which laterally displaces bracket 56 and permits loading and unloading of specimen 74 outside coils 80 and 81.

Deforming pressures are applied to L-shaped bracket 73, movable platen 72 and test specimen 74 by means of a hydraulic cylinder 94 which is rigidly secured to end plate 88. Cylinder 94 has a hollow piston 95 through which rod 96 extends. Pressure is exerted by piston 95 against firmly secured shoulder 97 on rod 96. A compression spring 98 is positioned between shoulder 97 and a hollow boss 99 which is secured to shell 54 and through which rod 96 extends. For sealing purposes, rod 96 passes through a bushing 100 and an O-ring 101, which are positioned in the wall of shell 54. The right end of rod 96 is positioned in opposition to a semi-spherical anvil 102 that is mounted on the second leg 76 of L-shaped bracket 73. In order to limit the travel of rod 96 and thereby control the extent of deformation of specimen 74, an adjustable stop mechanism is secured to the left end of rod 96. This stop mechanism consists of a sleeve 103 that is secured to rod 96 by means of pin 104. A nut 105 is adjustably positioned on the threaded end of sleeve 103. It will be appreciated that the relative axial position of nut 105 determines the extent of deformation of specimen 74, since axial displacement of rod 96 by piston 95 can occur only until nut 105 abuts end plate 88.

A series of six experiments is conducted employing the deformation dilatometer of FIG. 2, as well as six control runs employing the same dilatometer with conventional corderite platens which are otherwise identical to the fused silica platens described above. In each experiment, a solid cylindrical specimen of mild steel having a length of 6.5 mm and a diameter of 5 mm is first heated to 1200° C., at a uniform heating rate of 175° C. per second, and held at that temperature for three minutes. It then is allowed to cool by radiation to 950° C. where it is deformed to a length of 3.25 mm and, finally, its linear dimensional changes are measured while it is being quenched to room temperature at a uniform cooling rate of 150° C. per second. Neither the graphs of the recorded linear dimensional changes nor subsequent microscopic inspection of the fused silica platens reveal any evidence of distortion of the specimen bearing surfaces of the platens or of material migration across the platen/specimen interface. In contrast, all of the corderite platens show distortion of the specimen bearing surfaces, many being visible to the unaided eye. In addition, each of the graphs of the linear dimensional changes recorded after deformation with conventional corderite platens shows at least one anomalous curve break which is absent when deformation is effected with fused silica platens, but which otherwise is indistinguishable from a curve break reflecting an actual phase change.

Results similar to those demonstrated by monolithic fused silica platens also can be obtained with corderite or other ceramic platens that have had a layer of fused silica or quartz fused to the specimen bearing surface.

It will, of course, be understood that various additions and modifications may be made in the embodiments of this invention described above without departing from the spirit and scope of the invention as defined in the claims below.

The embodiments of the invention in which an exclusive property or privilege is claimed are defined as follows:

1. Deformation dilatometer comprising:
   (a) a linear variable differential transformer including an axially movable core coupled to a pushrod, an axially movable coil coupled to a separate pushrod and means for separately supporting each of said core and coil to permit independent axial movement thereof,
   (b) a pair of spaced apart specimen deforming platens having opposed parallel flat surfaces for supporting a test specimen therebetween, thereby forming an interface between each platen and said specimen, said surfaces being made of a material selected from fused silica and quartz to avoid microscopically visible migration of both said platen and said specimen across each said interface that would lead to anomalous dilatometer readings, one said platen being fixed and the other said platen being movable normal to said opposed parallel surfaces, one said pushrod being responsive to the cumulative linear expansion or contraction of said fixed platen and said specimen and the other said pushrod being responsive to the linear expansion or contraction of said fixed platen and
   (c) means for alternately applying a controlled specimen deforming force and a lesser non-deforming force to said movable platen in a direction normal to and toward said opposed parallel surfaces.

2. Deformation dilatometer of claim 1 including induction heating and gas quenching coils concentrically wound about said specimen.

3. Deformation dilatometer of claim 2 further including a fixed bracket for supporting said fixed platen and said linear variable differential transformer and a movable bracket for supporting said movable platen.

4. Deformation dilatometer of claim 3 further including means for axially displacing said linear variable differential transformer, said fixed bracket and said fixed platen to permit loading or unloading of the specimen outside said heating and quenching coils.

5. Deformation dilatometer of claim 1 further including a hermetically sealed housing for at least said specimen and said platens and means for evacuating said housing.

6. Deformation dilatometer of claim 1 wherein each said platen is made entirely of fused silica.

7. Specimen deforming platen for a deformation dilatometer, said platen having a smooth flat surface adapted to abut a dilatometer specimen, thereby forming an interface between said platen and said specimen and at least said smooth flat surface being made of a material selected from fused silica and quartz to avoid microscopically visible migration of both said platen and said specimen across said interface that would lead to anomalous dilatometer readings.

8. Deformation dilatometer platen of claim 7 wherein said platen is a single elongated piece of fused silica having said smooth flat surface on an end.

9. Deformation dilatometer platen of claim 8 including a lip contiguous with said smooth flat surface which is adapted to abut a dilatometer push rod.

10. Deformation dilatometer platen of claim 9 wherein said lip extends laterally from said elongated platen to provide clearance for a dilatometer pushrod that abuts said lip and is disposed adjacent and parallel to said platen.

11. Deformation dilatometer platen of claim 9 wherein said elongated platen has an axial groove in its side which terminates at said lip and provides clearance for a dilatometer push rod that abuts said lip and is disposed adjacent and parallel to said platen.

12. Deformation dilatometer platen of claim 9 wherein said platen is a cylinder having a flat side which terminates at said lip and provides clearance for a dilatometer pushrod that abuts said lip and is disposed adjacent and parallel to said platen.

13. Deformation dilatometer platen of claim 8 wherein said smooth flat surface is adapted to abut both said specimen and a dilatometer pushrod that is disposed parallel to and in tandem with said platen.

14. In a process for determining phase changes occurring during cooling of a mechanically worked ferrous metal specimen comprising holding said specimen between opposed parallel flat surfaces of a fixed specimen deforming platen and a movable specimen deforming platen thereby forming an interface between each platen and said specimen, deforming said specimen by applying a deforming force to said movable platen normal to and toward said parallel flat surfaces, reducing said force to a non-deforming level and measuring the relative movement of said parallel flat surfaces while cooling said specimen, the improvement comprising employing a material selected from fused silica and quartz for at least said parallel flat surfaces of said platens to avoid microscopically visible migration of both said platen and said specimen across each said interface that would lead to anomalous dilatometer readings.

15. In the process of claim 14, the improvement comprising employing platens, each of which consists of a single piece of fused silica.

* * * * *